(12) United States Patent
Whayne et al.

(10) Patent No.: US 8,267,951 B2
(45) Date of Patent: *Sep. 18, 2012

(54) DISSECTING CANNULA AND METHODS OF USE THEREOF

(75) Inventors: James G. Whayne, Chapel Hill, NC (US); Sidney D. Fleischman, Durham, NC (US); Christopher W. Sicvol, Durham, NC (US)

(73) Assignee: nContact Surgical, Inc., Morrisville, NC (US)

( * ) Notice: Subject to any disclaimer, the term of this patent is extended or adjusted under 35 U.S.C. 154(b) by 1008 days.

This patent is subject to a terminal disclaimer.

(21) Appl. No.: 12/174,549

(22) Filed: Jul. 16, 2008

(65) Prior Publication Data

US 2009/0312783 A1 Dec. 17, 2009

Related U.S. Application Data

(60) Provisional application No. 61/061,101, filed on Jun. 12, 2008.

(51) Int. Cl.
*A61B 17/94* (2006.01)
(52) U.S. Cl. ........................................ 606/190; 600/204
(58) Field of Classification Search .................. 600/101, 600/104, 115, 116, 204; 604/27, 28; 606/15, 606/40, 190, 192
See application file for complete search history.

(56) References Cited

U.S. PATENT DOCUMENTS

| | | |
|---|---|---|
| 3,470,876 A | 10/1969 | Barchilon |
| 4,040,413 A | 8/1977 | Ohshiro |
| 4,688,554 A | 8/1987 | Habib |
| 4,690,411 A | 9/1987 | Van Winkle |
| 4,719,924 A | 1/1988 | Crittenden et al. |
| 4,777,951 A | 10/1988 | Cribier et al. |
| 4,898,577 A | 2/1990 | Badger et al. |
| 4,920,980 A | 5/1990 | Jackowski |
| 4,921,482 A | 5/1990 | Hammerslag et al. |
| 4,960,134 A | 10/1990 | Webster, Jr. |
| 4,960,411 A | 10/1990 | Buchbinder |
| 4,976,688 A | 12/1990 | Rosenblum |
| 4,998,916 A | 3/1991 | Hammerslag et al. |
| 5,025,778 A | 6/1991 | Silverstein et al. |
| 5,030,204 A | 7/1991 | Badger et al. |
| 5,037,391 A | 8/1991 | Hammerslag et al. |
| 5,125,395 A | 6/1992 | Adair |
| 5,199,950 A | 4/1993 | Schmitt et al. |
| 5,203,767 A | 4/1993 | Cloyd |
| 5,205,816 A | 4/1993 | Dodson et al. |
| 5,235,966 A | 8/1993 | Jamner |

(Continued)

FOREIGN PATENT DOCUMENTS

WO WO 2007/037785 4/2007

OTHER PUBLICATIONS

Cragg, et al., "Endovascular diathermic vessel occlusion," *Radiology*, 144:303-308, 1982.

(Continued)

*Primary Examiner* — Theodore Stigell
*Assistant Examiner* — Gerald Landry, II
(74) *Attorney, Agent, or Firm* — Levine Bagade Han LLP (57) ABSTRACT

Methods and devices described herein facilitate improved access of locations within the body by providing a variety of dissection modes on a single access device.

13 Claims, 12 Drawing Sheets

U.S. PATENT DOCUMENTS

| | | | |
|---|---|---|---|
| 5,275,608 | A | 1/1994 | Forman et al. |
| 5,282,826 | A | 2/1994 | Quadri |
| 5,308,316 | A | 5/1994 | Williams et al. |
| 5,322,064 | A | 6/1994 | Lundquist |
| 5,325,845 | A | 7/1994 | Adair |
| 5,330,502 | A | 7/1994 | Hassler et al. |
| 5,374,277 | A | 12/1994 | Hassler |
| 5,378,234 | A | 1/1995 | Hammerslag et al. |
| 5,399,161 | A | 3/1995 | Williams et al. |
| 5,453,078 | A | 9/1995 | Valentine et al. |
| 5,460,621 | A | 10/1995 | Gertzman et al. |
| 5,571,088 | A | 11/1996 | Lennox et al. |
| 5,618,294 | A | 4/1997 | Aust et al. |
| 5,651,366 | A | 7/1997 | Liang et al. |
| 5,658,307 | A | 8/1997 | Exconde |
| 5,704,534 | A | 1/1998 | Huitema et al. |
| 5,725,523 | A | 3/1998 | Mueller |
| 5,783,227 | A | 7/1998 | Dunham |
| 5,785,706 | A | 7/1998 | Bednarek |
| 5,829,447 | A | 11/1998 | Stevens et al. |
| 5,843,017 | A | 12/1998 | Yoon |
| 5,865,802 | A | 2/1999 | Yoon et al. |
| 5,899,914 | A | 5/1999 | Zirps |
| 5,919,188 | A | 7/1999 | Shearon et al. |
| 5,967,997 | A | 10/1999 | Turturro et al. |
| 5,980,455 | A | 11/1999 | Daniel et al. |
| 6,077,287 | A | 6/2000 | Taylor |
| 6,080,151 | A | 6/2000 | Swartz et al. |
| 6,126,649 | A | 10/2000 | VanTassel et al. |
| 6,161,543 | A | 12/2000 | Cox et al. |
| 6,176,825 | B1 | 1/2001 | Chin et al. |
| 6,203,559 | B1 | 3/2001 | Davis et al. |
| 6,234,958 | B1 | 5/2001 | Snoke et al. |
| 6,264,654 | B1 | 7/2001 | Swartz et al. |
| 6,314,963 | B1 | 11/2001 | Vaska et al. |
| 6,330,965 | B1 | 12/2001 | Milliman et al. |
| 6,332,881 | B1 | 12/2001 | Carner et al. |
| 6,364,876 | B1 | 4/2002 | Erb et al. |
| 6,463,332 | B1 | 10/2002 | Aldrich |
| 6,478,028 | B1* | 11/2002 | Paolitto et al. ................. 128/898 |
| 6,484,727 | B1* | 11/2002 | Vaska et al. ................... 128/898 |
| 6,506,200 | B1 | 1/2003 | Chin |
| 6,514,250 | B1 | 2/2003 | Jahns et al. |
| 6,530,914 | B1 | 3/2003 | Mickley |
| 6,551,337 | B1 | 4/2003 | Rabiner et al. |
| 6,558,382 | B2 | 5/2003 | Jahns et al. |
| 6,592,547 | B2 | 7/2003 | Grimes et al. |
| 6,592,604 | B2 | 7/2003 | Hess et al. |
| 6,663,641 | B1 | 12/2003 | Kovac et al. |
| 6,666,854 | B1 | 12/2003 | Lange |
| 6,726,684 | B1 | 4/2004 | Woloszko et al. |
| 6,752,756 | B2 | 6/2004 | Lunsford et al. |
| 6,887,249 | B1 | 5/2005 | Houser et al. |
| 6,893,442 | B2 | 5/2005 | Whayne |
| 6,917,834 | B2 | 7/2005 | Koblish et al. |
| 6,953,454 | B2 | 10/2005 | Peterson et al. |
| 6,989,018 | B2 | 1/2006 | Fogarty et al. |
| 6,991,627 | B2 | 1/2006 | Madhani et al. |
| 7,001,404 | B1 | 2/2006 | Chin |
| 7,063,698 | B2 | 6/2006 | Whayne et al. |
| 7,144,363 | B2 | 12/2006 | Pai et al. |
| 7,300,448 | B2 | 11/2007 | Criscuolo et al. |
| 7,300,488 | B2 | 11/2007 | Szabo et al. |
| 7,328,071 | B1 | 2/2008 | Stehr et al. |
| 7,925,341 | B2 | 4/2011 | Fuimaono |
| 8,057,465 | B2 | 11/2011 | Sliwa et al. |
| 2002/0111637 | A1* | 8/2002 | Kaplan et al. .................. 606/139 |
| 2003/0229296 | A1 | 12/2003 | Ishikawa et al. |
| 2004/0039339 | A1 | 2/2004 | Magnusson |
| 2004/0143257 | A1 | 7/2004 | Fuimaono |
| 2004/0216748 | A1* | 11/2004 | Chin ............................. 128/898 |
| 2005/0203340 | A1 | 9/2005 | Butler et al. |
| 2005/0245789 | A1 | 11/2005 | Smith et al. |
| 2006/0009762 | A1 | 1/2006 | Whayne |
| 2006/0129132 | A1 | 6/2006 | Peterson et al. |
| 2006/0200124 | A1 | 9/2006 | Whayne et al. |
| 2006/0206113 | A1 | 9/2006 | Whayne et al. |
| 2006/0235381 | A1 | 10/2006 | Whayne et al. |
| 2006/0293646 | A1 | 12/2006 | Whayne et al. |
| 2007/0043351 | A1 | 2/2007 | Fleischman et al. |
| 2007/0083082 | A1* | 4/2007 | Kiser et al. .................... 600/115 |
| 2007/0083225 | A1 | 4/2007 | Kiser et al. |
| 2007/0219550 | A1 | 9/2007 | Thompson et al. |
| 2007/0244473 | A1 | 10/2007 | Thompson et al. |
| 2007/0249991 | A1 | 10/2007 | Whayne et al. |
| 2007/0250058 | A1 | 10/2007 | Whayne et al. |
| 2007/0255276 | A1 | 11/2007 | Sliwa et al. |
| 2007/0265595 | A1 | 11/2007 | Miyamoto et al. |
| 2008/0114288 | A1 | 5/2008 | Whayne et al. |
| 2008/0114342 | A1 | 5/2008 | Whayne et al. |
| 2008/0114354 | A1 | 5/2008 | Whayne et al. |
| 2008/0114355 | A1 | 5/2008 | Whayne et al. |
| 2009/0270676 | A1 | 10/2009 | Sicvol |

OTHER PUBLICATIONS

Gorisch et al "Heat-induced contraction of blood vessels" *Lasers in Surgery and Medicine*, 2:1-13, 1982.

Nath, et al., "Cellular electrophysiologic effects of hyperthermia on isolated guinea pig papillary muscle: implications for catheter ablation," *Circulation*, 88:1826-1831, 1993.

International Patent Application No. PCT/US2009/040981 in the name of Sicvol filed Apr. 17, 2009, International Search Report and Written Opinion mailed Jun. 11, 2009.

International Patent Application No. PCT/US2009/046780 in the name of Whayne et al. filed Jun. 9, 2009, International Search Report and Written Opinion mailed Jul. 28, 2009.

\* cited by examiner

DISSECTING CANNULA AND METHODS OF USE THEREOF

CROSS-REFERENCE TO RELATED APPLICATIONS

The present application is a non-provisional of U.S. Provisional Patent Application No. 61/061,101, filed on Jun. 12, 2008, the content of which is incorporated herein by reference in its entirety.

BACKGROUND OF THE INVENTION

Methods and devices for access devices to allow improved manipulation of organs and/or instruments within the body by creating working spaces within the body and adjacent to a target site. The methods and devices can be used in various parts of the body. One particular application includes the use of the access devices and methods to advanced devices to a surface of the heart to create atrial lesion patterns one or more atrial surfaces of the heart. Scope based surgical tools (e.g., elongated cannula/tubular devices that allow viewing of internal body tissues) provide surgeons with an ability to view a surgical site through a lens/fiber optic/camera of the scope and also provide an ability to access the surgical site through a working channel of the tool. In some cases, a scope permits the surgeon to access internal body tissue by passing the scope through a small diameter opening, port, or trocar placed in a surface of the body.

In many surgical procedures, the surgeon must also dissect tissue to gain access to the intended target site. For example, U.S. Pat. No. 5,205,816 (the entirety of which is incorporated by reference) teaches a simple blunt dissector having a cannulated single lumen device with a mandrel inserted into the device for carrying a simple textured cloth that provides a textured surface. However, such basic devices are used in addition to the scopes that are used for such minimally invasive procedures. The additional blunt dissector requires an additional entry port or must be exchanged with other tools that are advanced through the entry site. In addition, a physician must manipulate a scope as well as the blunt dissection device.

Increasingly, scopes are being adapted to assist in the dissection of tissue to eliminate the need for an additional dissection device. Clearly, doing so reduces the number of devices that a physician must manipulate in the surgical area as well as the number of devices that are advanced through the body opening/port/incision. Many conventional devices rely upon balloon-type structures for dissection of tissue via expansion of the balloon or close-ended obturator-type structures that dissect via dilation via insertion of the closed end.

For example, U.S. Pat. No. 6,989,018 to Fogarty et al. (the entirety of which is incorporated by reference herein) discloses a balloon dissection apparatus having an elongate balloon that performs the tissue dissection. However, because this dissection relies upon somewhat uncontrollable expansion of the balloon (as the internal balloon pressure increases), the physician typically has less control over the amount of tissue dissection as compared to using a non-expanding structure to physically dissect tissue.

While obturator type devices avoid the problems with somewhat unpredictable dissection via balloon expansion, such devices are still not optimal. For example, U.S. Pat. Nos.: 6,592,604; 6,752,756; and 7,001,404 (the entirety of each patent incorporated by reference herein) describe tissue dissection devices having with closed ends (where such ends act as obturators). The closed ends are generally translucent to allow for visualization therethrough. Yet, dissection of tissue occurs via dilation of the tissue using the closed end. U.S. Pat. No. 7,300,448 (the entirety of which is incorporated by reference herein) discloses a combination balloon dissector having an obturator associated with the balloon dissector assembly.

In any event, the balloon dissection or dissection via obturator dilation as described above do not provide the physician with the ability to tease or loosen adjoining tissue for a more controlled dissection of tissue.

Another drawback with conventional devices is their failure to accommodate removal of debris that is generated by the tissue dissection process. Such debris interferes with visualization through the scope. For example, during tissue dissection the resultant blood often smears the visualization scope. Alternatively, tissue debris (e.g., fatty deposits, etc.) present at the surgical site adheres to the visualization element. Even bodily fluids and the inherent body temperature can combine to produce condensation over the visualization scope. Often, a separate irrigation source must flush the distal end of the scope to maintain proper visualization. For example, U.S. Pat. No. 6,176,825 (incorporated by reference herein) discloses a cannula based irrigation system having a separate moveable irrigation member within the device.

Without the ability to irrigate the scope, a physician will be forced to repeatedly remove the scope from the surgical site and body for cleaning. Removal and cleaning of the scope increases the length and therefore the risk associated with the surgical procedure. Moreover, apart from the debris, in the obturator-type devices described above, the closed transparent end of the device often causes a distorted view of the working area.

Atrial fibrillation surgery is one example of a surgical procedure that relies upon dissection of tissue to access the target tissue site. To access the fibrillation surgery site, a physician typically dissects through tissue under direct visualization using an endoscope. Preferably, once the physician reaches the target site, the physician will establish a working channel or access path to the target site for the advancement of various surgical devices.

Accordingly, there remains a need for improved access devices that are configured to aid a physician during dissection of various tissues to access a target tissue site by providing the ability to gently dissect as well as establish space required to perform the intended procedure. The improved methods and devices described herein offer improved access to tissue regions within the body, especially those organs in the thoracic cavity. However, the devices and methods have applicability to any region in the body apart from the thoracic cavity.

For convenience, the following disclosure makes reference an endoscope as the scope based device. However, the inventive devices and methods described herein specifically include the use of any number of scope based devices generally similar to an endoscope; for example, any type of rigid or flexible tube with a light delivery system and a visualization source that transmits an image to the viewer, and (optionally) a working channel or lumen that permits delivery of an additional device through the scope.

SUMMARY OF THE INVENTION

The devices and methods described herein allow for accessing various regions of the body by using a multi-mode dissection device. While features of the device provide the ability to access posterior regions of the thoracic cavity, the devices can be used in a variety of medical procedures.

In one variation, the device comprises a multi-mode tissue dissecting device for delivering one or more medical devices to a target site. Variations of the devices include a cannula having a working channel extending therethrough and exiting at a distal opening, where the distal opening permits movement of the medical device in a direction parallel to an axis of the working channel; a dilation wedge, smaller than an outer diameter of the cannula and located at a distal end of the cannula and configured to permit mechanical dilation of a small opening in tissue into a larger opening as a first dissection mode; a dissecting surface located on a portion of the dilation wedge, the dissecting surface having a frictional coefficient greater than that of a frictional coefficient of the cannula such that the dissecting surface grips the tissue as the dissecting surface moves against the tissue to permit dissection of tissue as a second dissection mode; and an expandable dilation member located about an exterior surface of the cannula to separate tissue when expanded as a third dissection mode.

Descriptions of the varying dissection modes are discussed below. However, the varying modes allow for gentle dissection, gradual dilation dissection, as well as a more forceful dissection by expansion. The latter dissection mode is useful to create a cavity between adjacent body structures or organs.

While the examples described herein generally place the wedge dissection mode and the frictional dissection mode on a tip of the device, variations of the device include such dissection modes placed on various other regions of the cannula. For example, a dissection surface can be placed on an exterior of the expandable dilation member of the device.

In additional variations, the device shall include at least one fluid port located within the working channel configured to apply suction or deliver a fluid within the working channel, the fluid port in fluid communication with a fluid lumen within the cannula. The fluid lumen can be located within a wall of the cannula and where the fluid port is located in the wall of the cannula As disclosed below, a number of fluid ports can be located in the working channel and adjacent to the dilating wedge. The dilating wedge can itself comprise a beveled tip of the cannula. The fluid ports can be located within the beveled tip portion or further proximal within the working channel. The plurality of fluid ports can be aligned along an axis of the working channel to provide a greater area of perfusion and vacuum. In additional variations, one or more fluid ports can be placed on an exterior of the cannula.

Regarding the dilation wedge, the device can be fabricated so that the dilation wedge comprises a transition surface extending from the dilation wedge to an exterior surface of the cannula. The transition surface can be smooth to gradually dilate a small opening in tissue into a larger opening.

The cannula of the present device can be fabricated for rigidity or flexibility depending on the desired application. In any case, the cannula body shall have column strength sufficient to advance the cannula into the body without collapsing. In alternate variations, the cannula can include a shapeable support member located in the cannula, where the shapeable support member causes the cannula to retain a shape of the shapeable support member.

In another variation of a dissecting access device, the dissecting access device comprises a cannula having a working channel extending therethrough and exiting at a distal opening, where the distal opening allows movement of the medical device through the distal opening and parallel to an axis of the working channel; a dilation wedge located at a distal end of the cannula and configured to permit dilation of a small opening in tissue into a larger opening; a dissecting surface located on a portion of the dilation wedge, the dissecting surface having a frictional coefficient greater than that of a frictional coefficient of the cannula such that the dissecting surface grips the tissue as the dissecting surface moves against the tissue to permit dissection of tissue; at least one fluid port located within the working channel configured to apply suction or deliver a fluid within the working channel, the fluid port in fluid communication with a fluid lumen within the cannula; and a gripping portion having an open proximal end allowing for advancement of the medical device therethrough and a first fluid connector for coupling the fluid lumen to a fluid source.

The invention also includes methods of use of the device described herein. In one unique application the device allows for creation of atrial lesion patterns on first and second atrial surfaces of a heart of a patient. Such a method includes accessing a diaphragm through a first incision in an abdomen of the patient; advancing at least a first and second access devices through the diaphragm into a thoracic cavity of the patient and into a pericardial space adjacent to the first atrial surface; positioning a coagulation device adjacent to the first atrial surface through one of the access devices; creating a first coagulation region on the first atrial surface with the coagulation device; dissecting a pericardial reflection with a dissecting surface of the first access device so that a second atrial surface is accessible from the first atrial surface; and creating a second coagulation region on the second atrial surface with the coagulation device.

The method further includes advancing at least the first and second access devices through the diaphragm and adjacent to the first atrial surface without creating an incision in a chest or through a rib cage of the patient.

The method also allows for the dissection of pericardial reflections by rotating the first access device so that the dissecting surface of the access device gently dissects the pericardial reflection. Additional variations of the method include a first pericardial reflection, then advancing the first access device adjacent to a pair of right pulmonary veins and further dissecting a second pericardial reflection adjacent to a transverse sinus of the heart.

The methods allow for creating the first coagulation region on the first atrial surface with the coagulation device by creating a series of coagulation lines to isolate a right and a left pair of pulmonary veins. Then the physician can advance an access device adjacent to the second atrial surface prior to creating the second coagulation region. Once on the second atrial surface, the method can include creating a third coagulation region across the first and second atrial surfaces and through at least one of the dissected pericardial reflections.

In a further variation, the method can include further comprising advancing the coagulation device from the first atrial surface to the second atrial surface through at least one of the dissected pericardial reflections to create the third coagulation region.

Ultimately, the method comprises creating a bi-atrial lesion pattern where coagulation lesions on the left and right atrial surface can intersect.

The subject matter of this application may be incorporated with the subject matter in the following commonly assigned published applications entitled DIAPHRAGM ENTRY FOR POSTERIOR SURGICAL ACCESS: US20070083082A1; US20070083225A1; US20070249991 A1; US20080114342A1; and US20080114288A1; as well as U.S. patent application Ser. No. 12/108,426 entitled ARTICULATING CANNULA ACCESS DEVICE and filed on Apr. 23, 2008; the entirety of each of which is hereby incorporated by reference.

Variations of the access device and procedures described herein include combinations of features of the various embodiments or combination of the embodiments themselves wherever possible.

DETAILED DESCRIPTION

Methods and devices described herein provide for improved manipulation of organs and/or instruments within the body by creating working spaces within the body and adjacent to a target site. While the following disclosure discusses devices and methods for use in the thoracic cavity, such methods and devices can be applied to various body portions outside of the thoracic cavity. The methods and devices may allow for direct visualization along regions of anatomic structures not attainable with conventional approaches.

Furthermore, the methods and devices described herein may be used in conjunction with, or as an alternative to the conventional approaches described herein. For example, while some surgical approaches and procedures described herein rely on entry through the diaphragm of a patient to access a regions of the thoracic cavity, the surgical approaches and procedures can be combined with various other access methods.

Figure 1:
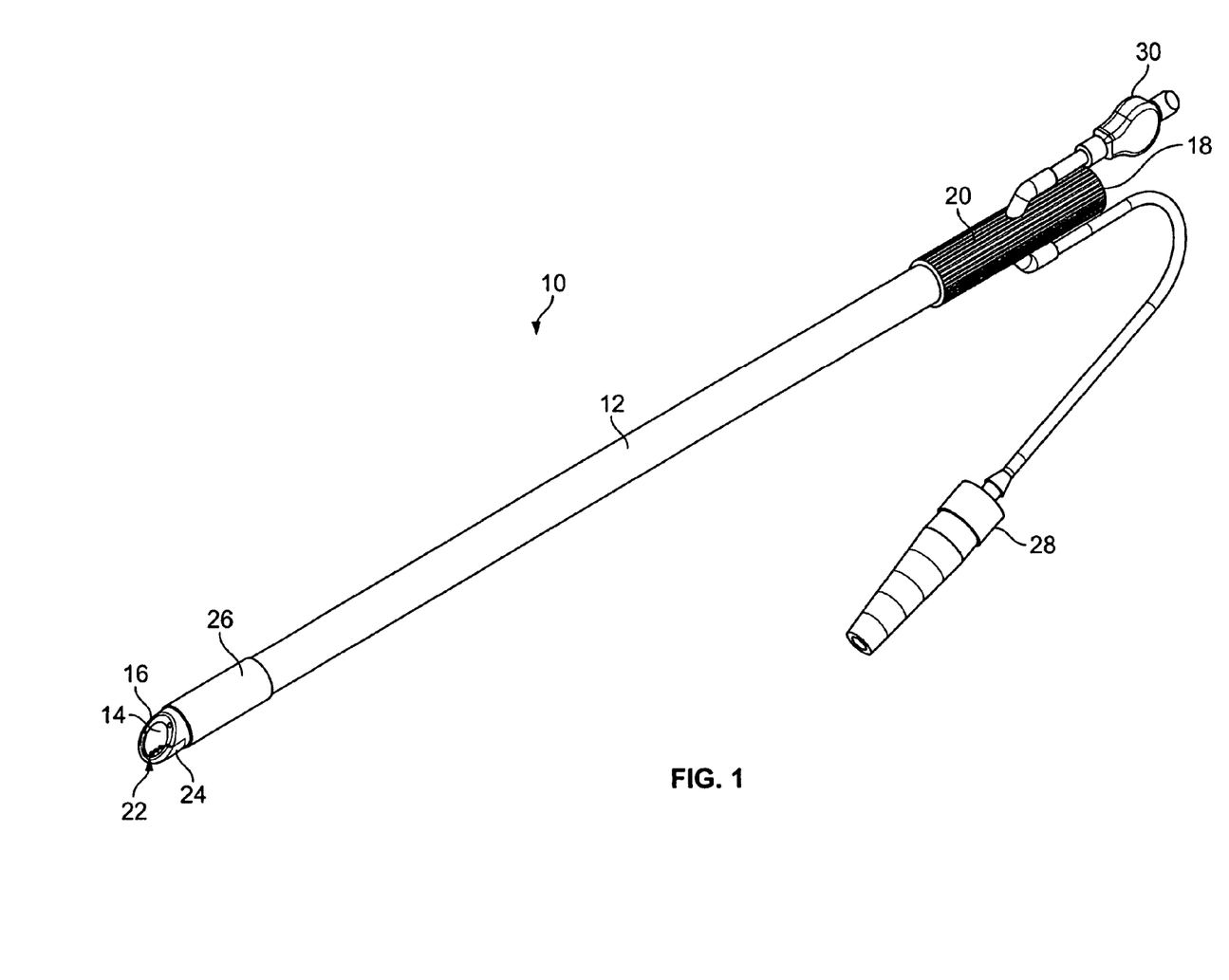
FIG. 1 shows one example of a tissue dissection access device configured to dissect tissue using a number of different tissue dissection modalities.

FIG. 1 shows one example of a tissue dissection access device 10 configured to dissect tissue using a number of different tissue dissection modalities. As described above, devices according to the present invention that provide a number of dissection modalities, e.g., frictional dissection, wedge-type dissection, and dilation type dissection, provides a physician with a number of options to access a target site during a minimally invasive procedure.

FIG. 1 shows a device with several tissue section modalities. However, certain variations of devices within the scope of this invention can have any sub-combination of tissue dissection modalities.

Turning now to the illustrated variation, the first dissection modality comprises a dilation wedge tip 22 or beveled tip located at the distal end of the cannula 12. The wedge shaped tip provides a mechanical wedge dissection modality as the tip 22 can be inserted into small openings in tissue and where advancement of the tip 22 mechanically dilates the opening.

The second dissection mode comprises a dissection surface 24 located on a side of the dilation wedge 22. The dissection surface 24 provides a frictional or abrasion dissection modality as the physician is able to apply the tip to a tissue surface and gently dissect the tissue apart by relying upon the increased friction between the dissection surface 24 and the tissue. The dissection surface 24 can dissect tissue via axial movement relative to the tissue, by rotational movement, or a combination thereof. In certain variations, the dissection surface 24 can be configured to dissect tissue when moved in a single direction (as discussed below). For example, the dissection surface 24 can be configured to catch tissue as it is pulled in a proximal direction. This allows distal advancement without resistance. In any case, as the surface 24 moves against tissue, the increased friction of the surface 24 catches on tissue to gently separate fibers of soft tissue. Although the variations shown herein depict the dissection surface on an end of the dilation wedge 22, the dissection surface 24 can be located on the cannula surface or even on a balloon dilation surface.

The third dissection mode comprises an expandable dilation balloon member 26 located on a surface of the cannula 12. The dilation balloon member can be a distensible or non-distensible balloon. Generally, the dilation balloon member 26 can be used to create a temporary cavity or to separate tissue to a greater degree than a diameter of the cannula 12. Any number of expandable members can be used in place of a balloon (e.g., a mechanical basket, axially aligned flexible strands, an expandable helical wrapped ribbon or wire, etc.)

FIG. 1 also shows another feature of certain devices that provides a physician with unobstructed access to tissue sites that are exposed by tissue dissection. As shown in FIG. 1, the device 10 includes a cannula 12 having a working channel 14 extending therethrough and terminating at a distal opening 16. In certain devices the distal opening 16 is in-line with an axis of the working channel 14. This feature provides an ability to extend a medical device through the working channel 14 and directly into or adjacent the tissue being dissected. Such a feature is very beneficial when using the working channel to visualize tissue being or using the working channel to advance a device therethrough to treat a tissue site that is exposed by dissected tissue.

Accordingly, a physician can advance any such medical device from a proximal end 18 of the device 10 (as shown the device has an optional handle portion 20 on a proximal end) through the distal opening 16 and move the medical device relative to the distal opening 10 in alignment with an axis of the working channel 14 of the access device 10. The handle can be configured to provide a textured surface to allow a physician to grip and manipulate the device.

The cannula shaft (or the portion of the cannula 12 between the wedge tip 22 and the proximal portion 18 or handle portion 20) can be constructed to have a number of different configurations. For example, the cannula shaft can be flexible such that it can be deflected from an axis of the distal opening 16. However, the cannula shaft shall have a column strength that allows a physician to push or advance the device into tissue or between organs. In some cases, the flexibility of the shaft allows flexion when medical devices are placed therethrough. This can reduce forces placed on the target tissue. Alternatively, use of rigid medical devices placed within the working channel 14 can change the flexibility of the shaft to increase the ease by which the device 10 is remotely manipulated within the body. The cannula 12 can be fabricated from any variety of medical grade materials. In one variation, the cannula is constructed from either silicone or C-Flex.

The device 10 also includes any number of fittings to couple the device to a fluid or vacuum source. As shown, the device 10 includes a first fluid connector 28. In this variation, the fluid connector 28 can be connected to a vacuum or fluid source to remove fluids from the working channel 14 of the device or deliver fluids to the working channel 14. The fluid connector 28 can also be connected to a vacuum source and fluid source simultaneously via the use of a two way valve or similar type of flow diverters (e.g., a two way stop cock). In those variations of the device 10 including an expandable dilation member 26, a separate connector 30 can be provided to couple the dilation member 26 to a source of pressure (either air or fluid).

Figure 2A:
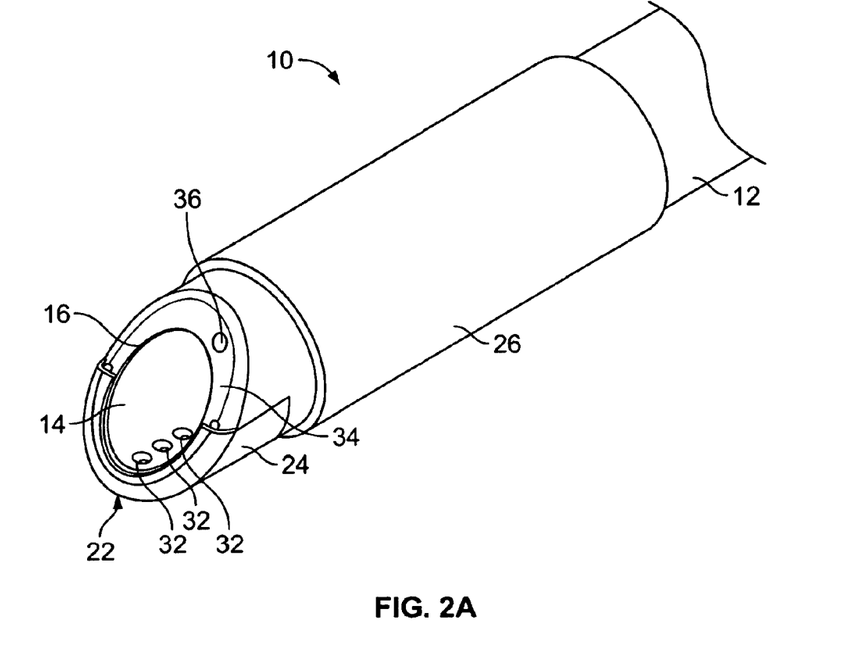
FIG. 2A depicts a magnified view of a working end of the device of FIG. 1.

FIG. 2A depicts a magnified view of a working end of the device 10 of FIG. 1. As shown, the working channel 14 also includes a plurality of fluid ports 32 located therein. As noted above, the fluid ports 32 are coupled to a fluid source for delivering a fluid to irrigate the target tissue or a medical device located within the working channel 14. The fluid ports 32 also allow a physician to remove debris or fluid from the working channel 14.

In the variation of the device 10 shown, there are a number of fluid ports 32. Additional variations of the device include a single fluid port 32. However, multiple fluid ports 32 provide an advantage to generate a larger area of fluid flow within the working channel 14. Such a feature improves the ability of the device 10 to clean a medical device located therein by providing a greater area to deliver or remove fluid. In the variation shown, the fluid ports 32 are located within the bevel of the dilation wedge 22 and are placed in alignment along an axis of the working channel 14. However, the fluid ports 32 can also be arranged in a non-aligned manner or a random pattern. In addition, variations of the device 10 include fluid ports arranged on an exterior of the cannula 12 or proximal to the dilation wedge tip 12 within the working channel 14.

FIG. 2A also depicts additional aspects of the device 10. As shown, the dilation wedge 22 comprises a transition surface 34 along the distal opening 16 that provides a smooth transition to the outer surface of the cannula 12. This feature aids in dilating tissue from a small opening to a larger opening that is the size of the outer diameter of the cannula 12. FIG. 2A shows another optional feature of a visualization element 36 located on a front face of the device 10. Such elements can include a fiber optic scope or line as well as a CCD camera or any such visualization component as commonly known and used with various medical scopes.

In addition, although the working channel 14 and distal opening 16 are frequently depicted as having a circular cross section, variations of the device contemplate the working channel 14 and distal opening 16 to have non-cylindrical openings. For example, the cross-sectional profile can include oval or rectangular shapes where a height and width of the channel are not equal. The benefit of such configurations is that multiple devices can be advanced parallel within the working channel.

Figure 2B:
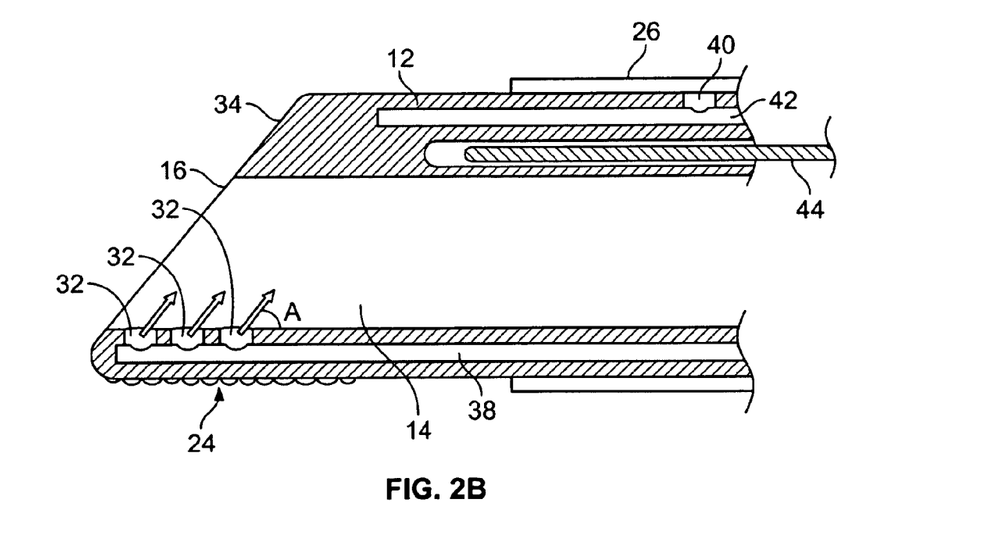
FIG. 2B shows a partial cross sectional view of a variation of a working end of a tissue dissection access device.

FIG. 2B shows a partial cross sectional view of a variation of a working end of a device 10 according to the present invention. As shown, the device 10 includes a plurality of fluid lumens 38, 42 coupled to respective fluid ports 32, 40. As noted above, fluid ports 32 can be placed in fluid communication with the working channel 14 to irrigate and remove fluids to or from the channel 14 for the clearing of debris from medical devices advanced within the working channel 14. One or more fluid ports 40 also can be placed within the expandable dilation member 26 for pressurization of the member 26 to dissect or separate tissue. In certain variations, the fluid ports 32 located within the working channel 14 are angled or directed towards a proximal end of the device 10 (e.g., such that an axis of the port 32 forms an angle A that is less than 90 degrees. Directing the ports 32 in such a manner permits fluid to be delivered to the face of any device advanced within the working channel.

FIG. 2B also shows an optional support member 44 located within a wall of the cannula 12. The support member can be rigid or shapeable. A malleable or shapeable support 44 may be incorporated into a portion or an entirety of the cannula 12 to allow shaping the member into a desired configuration. The shape is selected to improve the ability of the device to direct the scope and instruments towards the desired site within the body (e.g., a region of the surface of the heart, or other anatomic structure). The support 44 can be placed in a support lumen such that the support 44 is slidable within the support lumen of the cannula 12. The support 44 can be removable from the cannula 12. In certain variations, it may be desirable to minimize a wall thickness of the cannula 12 to maximize the working channel 14 diameter and minimize the outer diameter of the cannula 12. In such a case, the device will not be constructed to have a support member 44 or will not have the visualization element 36 shown in FIG. 2A.

FIGS. 3A to 3D show variations of different dissecting surfaces 24 for use with devices as described herein. In some variations a device can be equipped with more than one type of dissecting surface 24. Moreover, a dissecting surface 24 can be placed on any portion of the device (including the expandable dilation member 26). Although the figures illustrate the dissecting surfaces 24 on the bottom edge of the cannula 12, the dissecting surfaces can extend over a full or partial perimeter of the cannula surface 12.

Figure 3A:
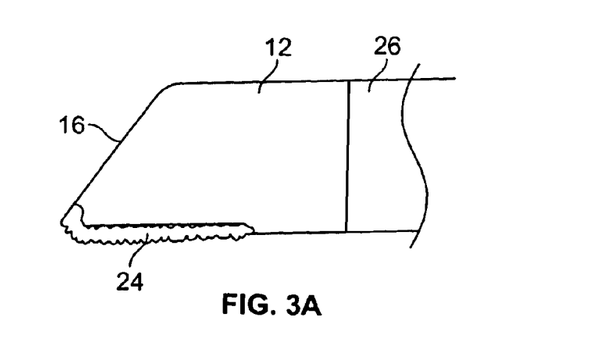
FIGS. 3A to 3D show variations of different dissecting surfaces for use with devices as described herein.

FIG. 3A shows a variation of a dissecting surface 24 that comprises a layer of material, such as a polymeric layer, a layer of cloth, or other surgical material that is textured and can be used to abraid tissue for dissection. In an additional variation, the material can comprise an absorbable surgical sponge material, such as gauze or other woven cotton. Alternatively, the material can be comprised of a polymeric material that is inserted into or onto the cannula 12 where the polymeric material comprises a sufficiently high coefficient of friction that the nature of rubbing the material against tissue results in abrasion and dissection of the tissue. The texture of the material abrades the tissue being dissected so that the dissection can be performed in either a distal or proximal motion of the cannula 12.

The cannula 12 can have a relief section removed for insertion of the material 24. In alternate variations, the material can be affixed to an exterior of the device. In certain variations, the material is non-absorbent and retains texture and stiffness as it encounters body tissue and fluids. The material can be glued onto the cannula 12 or the cannula 12 can have a textured or sharp surface to retain the material.

Figure 3B:
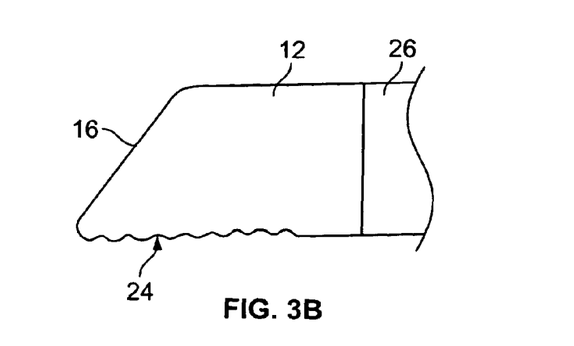

FIG. 3B shows another variation of a dissection surface 24. In this example, the dissection surface 24 is formed directly into the surface of the cannula 12 via a mechanical or chemical process. For example, the cannula 12 can be grounded, etched, swaged, bead-blasted, heat formed, etc. Alternatively, the textured dissection surface 24 could be formed in a mold such that the dissection surface 24 is directly molded onto the cannula 12.

Figure 3C:
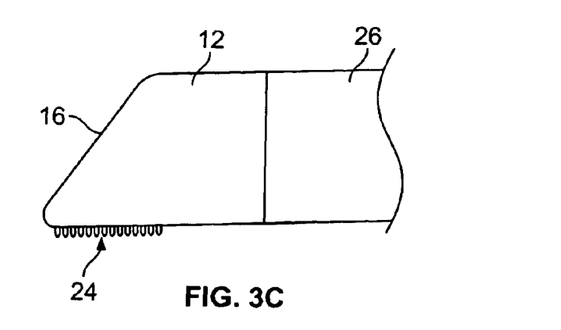

FIG. 3C shows another variation of a dissection surface 24 formed from a plurality of surfaces that extend from a surface of the cannula 12. For example, the surface 24 can be formed from granules deposited on the cannula 12 to form a sandpaper like coating. Alternatively, the surface 24 can comprise flexible extensions that engage and grip tissue when moved across the tissue.

Figure 3D:
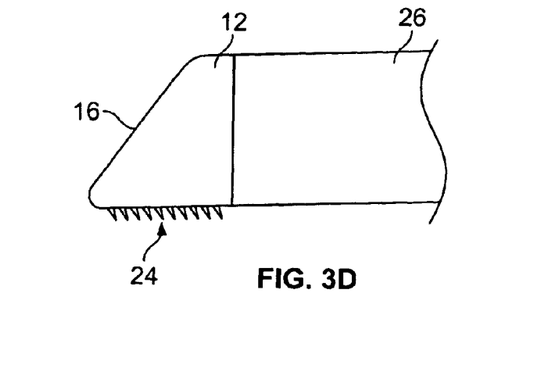

FIG. 3D shows yet another variation of a dissecting surface 24. In this variation, the dissecting surface 24 comprises a directional dissecting surface 24 as shown by the saw-tooth configuration. The dissecting surface 24 generally does not engage the tissue when moved in a first direction (in this case a distal direction) but engages tissue when moved in a second direction (in this case a proximal direction).

Figure 4A:
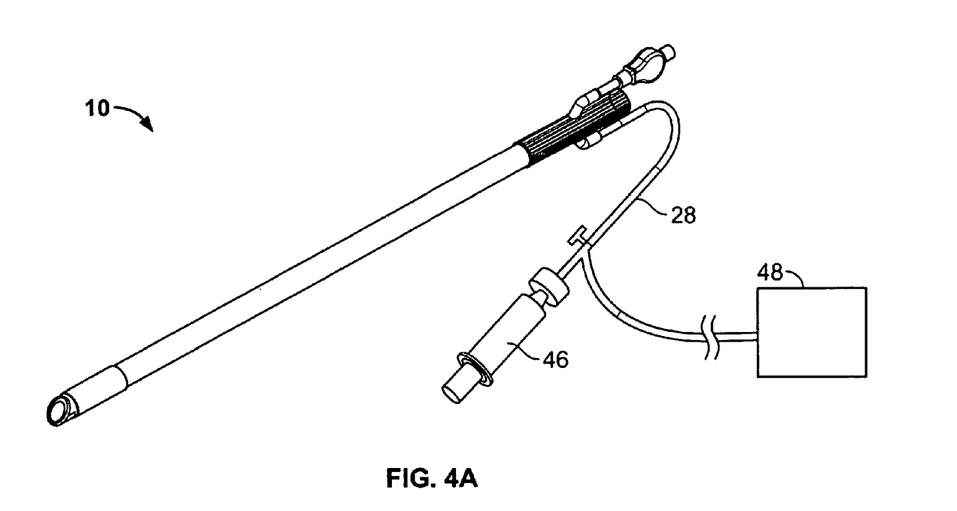
FIG. 4A illustrates a variation of a tissue dissecting device coupled to a syringe and vacuum source.

FIG. 4A illustrates a variation of a tissue dissecting device 10 coupled to a syringe 46 via a connector 28. Optionally, the device 10 can be simultaneously coupled to a vacuum source 48 via a two way valve.

Figure 4B:
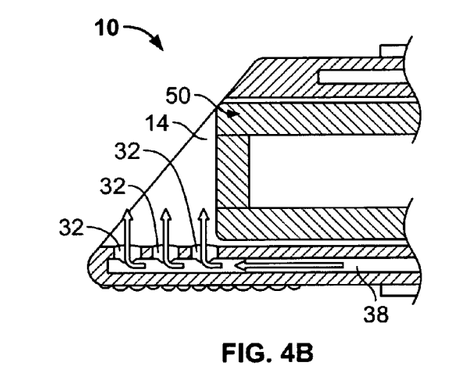
FIGS. 4B and 4C show irrigation and removal of fluids through ports in a working channel of a dissection access device.
Figure 4C:
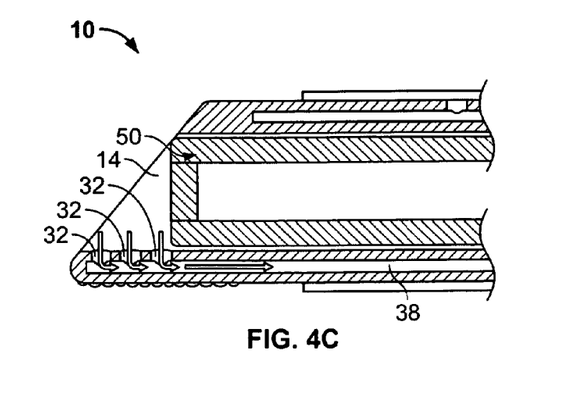

As described herein, the device 10 can accommodate a scope or medical device 50 such as an ablation device. Regardless of the medical device, as the tissue dissecting device 10 dissects tissue, various bodily debris and fluid often attach to the medical device advanced therethrough. In the case of a scope, the debris and fluid can prevent the scope from providing a clear image to the physician. In the case of energy delivery devices, debris attached to an energy transfer element can affect the energy transfer that should otherwise occur. As shown in FIG. 4B, injection of fluid through the fluid lumen 38 and fluid ports 32 into the working channel 14 bathes the end (or other area as appropriate) of the medical device 50 removing the debris and cleaning the device 50. FIG. 4C shows a state of the device 10 where suction is applied through the fluid lumen 38 to draw fluid and other debris into the fluid ports 32. Placement of the fluid ports 32 within the working channel 14.

Figure 5A:
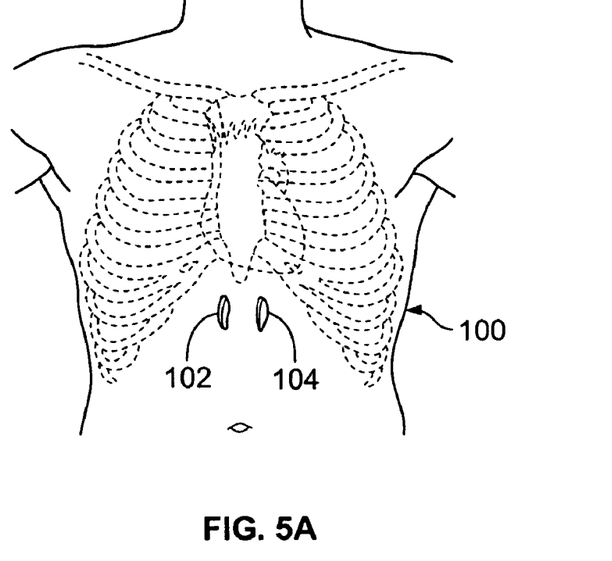
FIGS. 5A and 5B illustrate placement of a pair of devices within a body of a patient in an exemplary procedure to access a posterior region of the thoracic cavity.
Figure 5B:
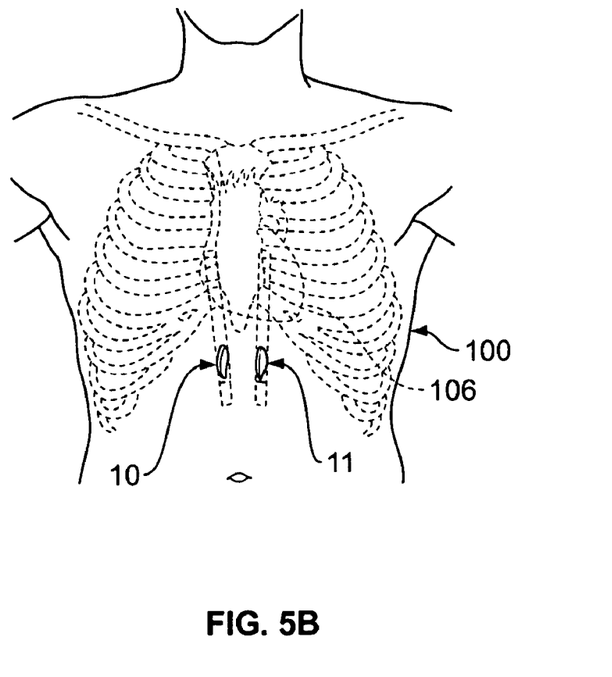

FIGS. 5A and 5B illustrate placement of a pair of devices 10 within a body 100 of a patient in an exemplary procedure. It is noted that the device 10 can be used in any part of the body and through any incision or port in a minimally invasive manner. However, the device 10 can also be used in open surgical procedures.

FIG. 5A illustrates creation of two incisions 102 104 in the body 100. In the illustrated example, the incisions are made in the abdomen of the patient so that the dissecting access devices 10, 11 can then pass through a diaphragm of the patient to a posterior side of the thoracic cavity (as shown in FIG. 5B).

Figure 6A:
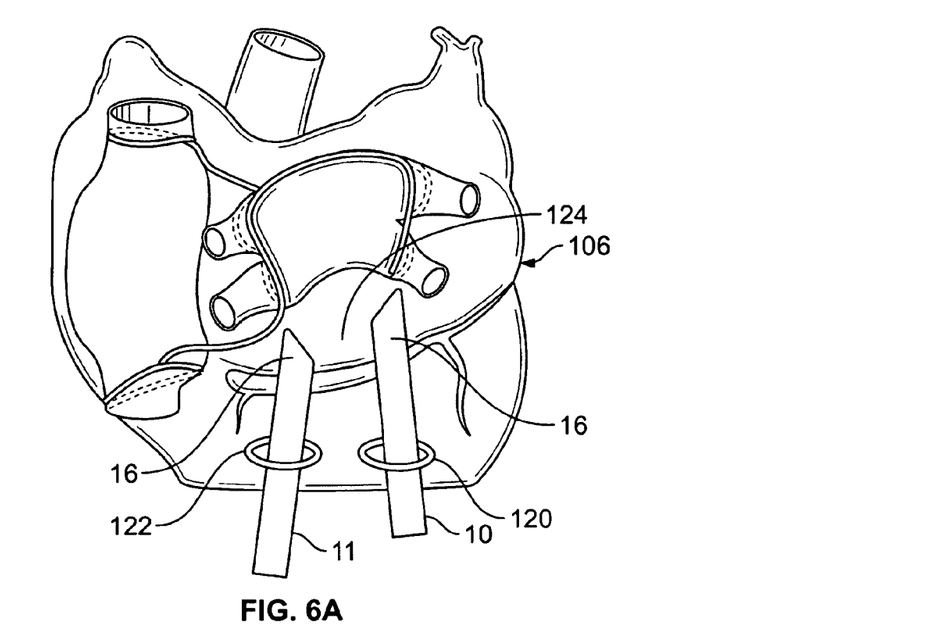
FIGS. 6A to 6Q show one exemplary use of the dissection access devices described herein to create bi-atrial lesion pattern on a posterior region of the heart.
Figure 6B:
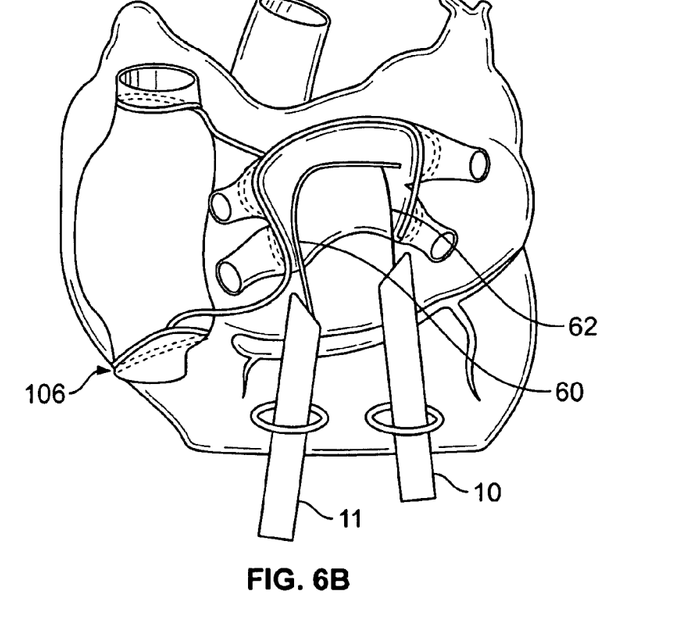
Figure 6C:
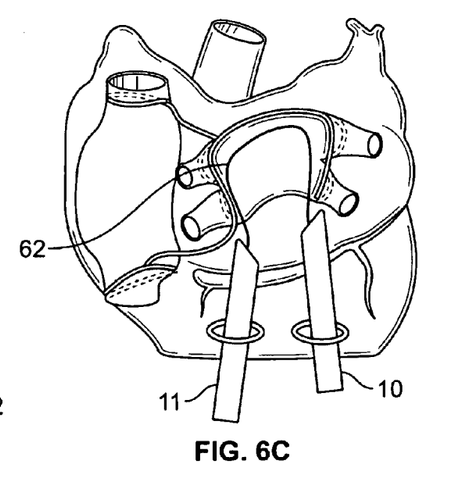
Figure 6D:
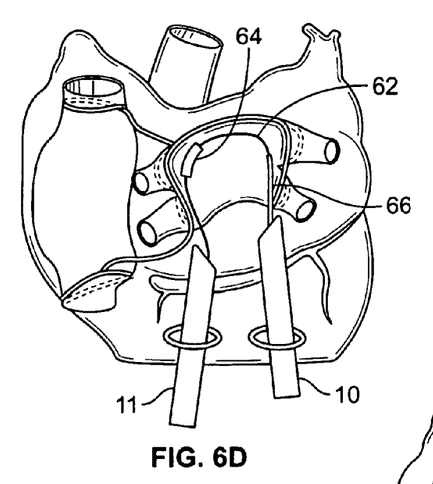
Figure 6E:
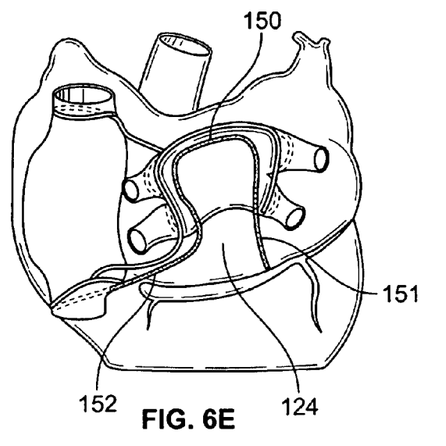
Figure 6F:
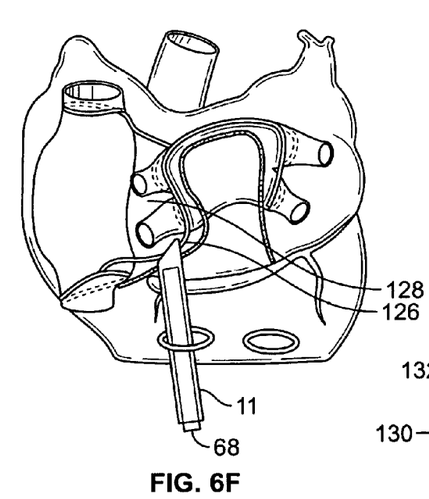
Figure 6G:
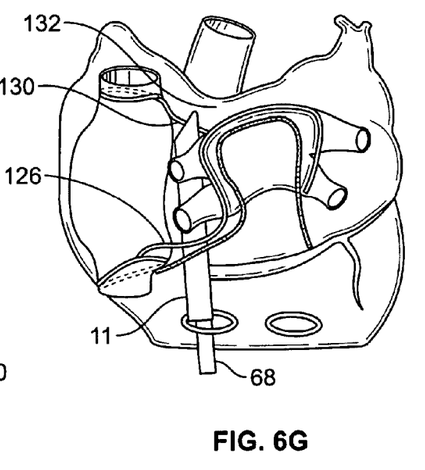
Figure 6H:
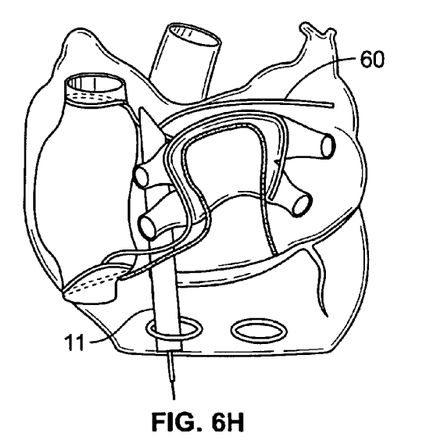
Figure 6I:
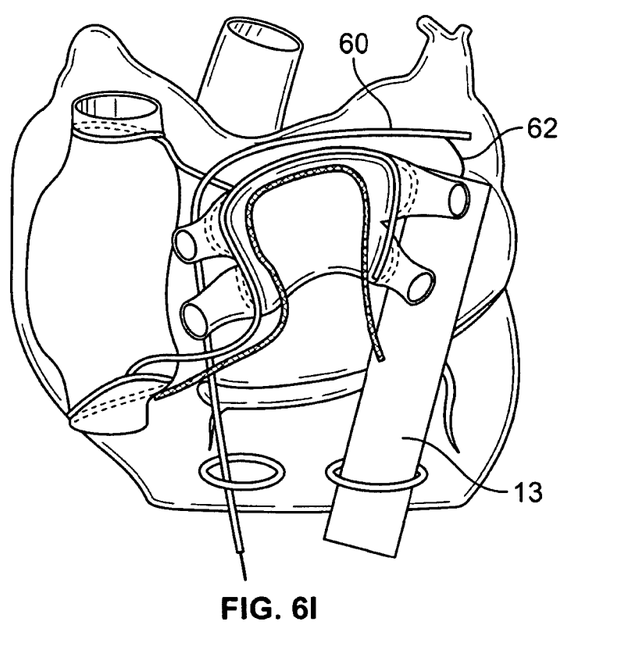
Figure 6J:
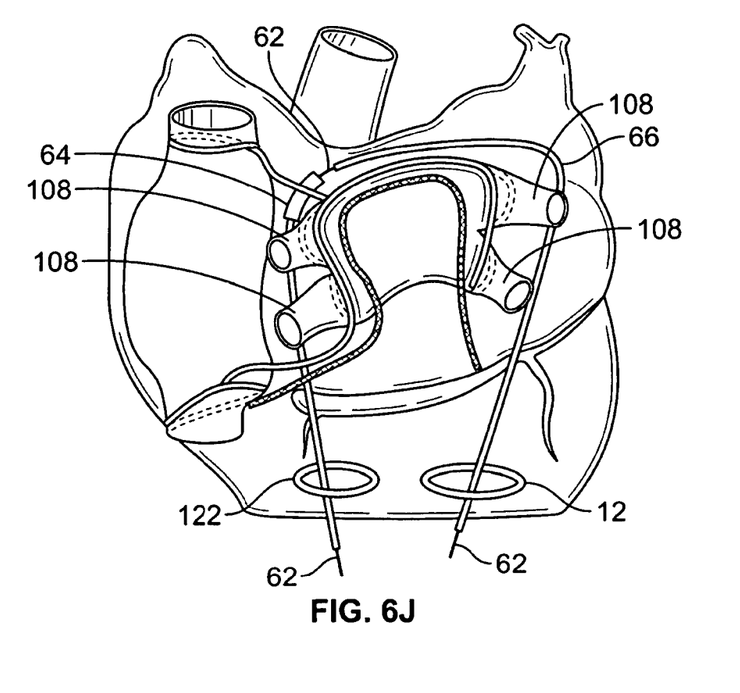
Figure 6K:
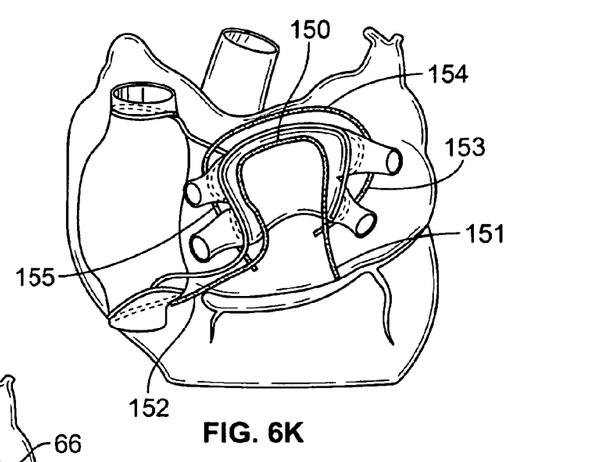
Figure 6L:
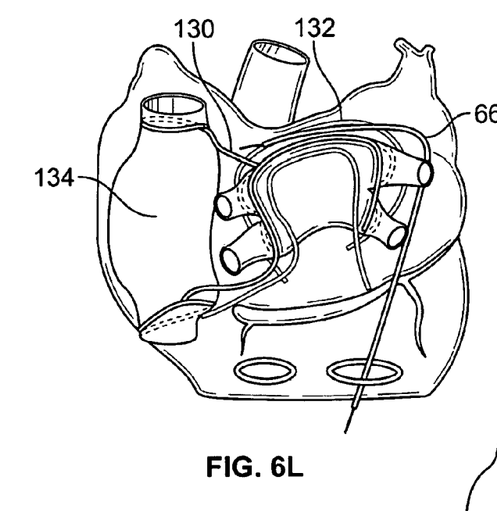
Figure 6M:
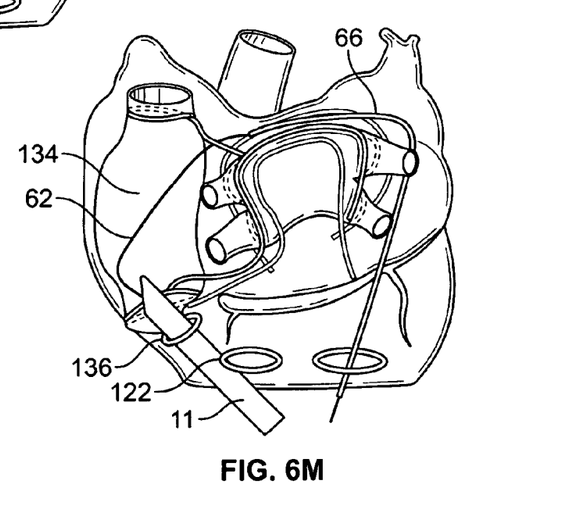
Figure 6N:
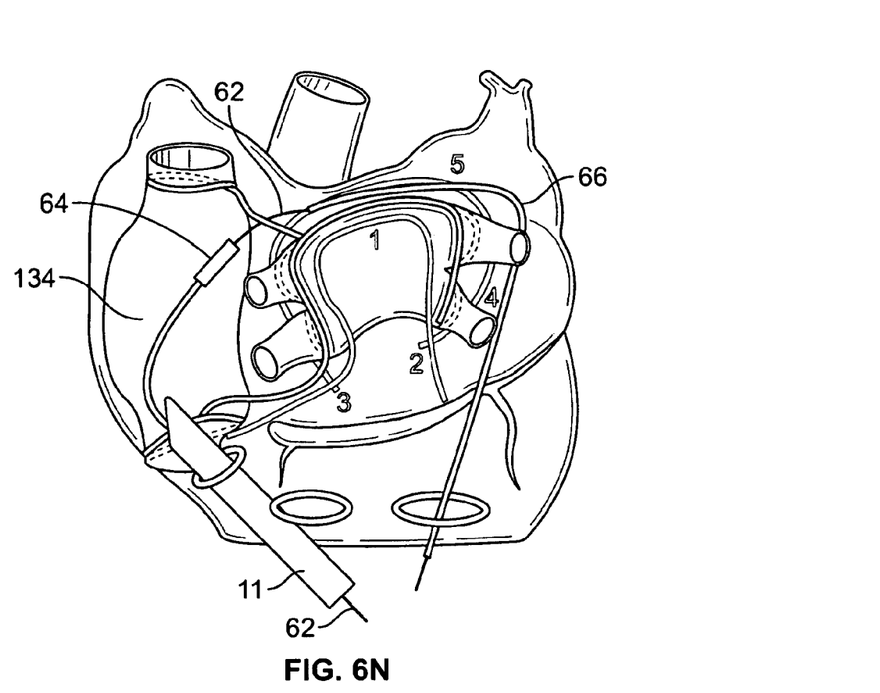
Figure 6O:
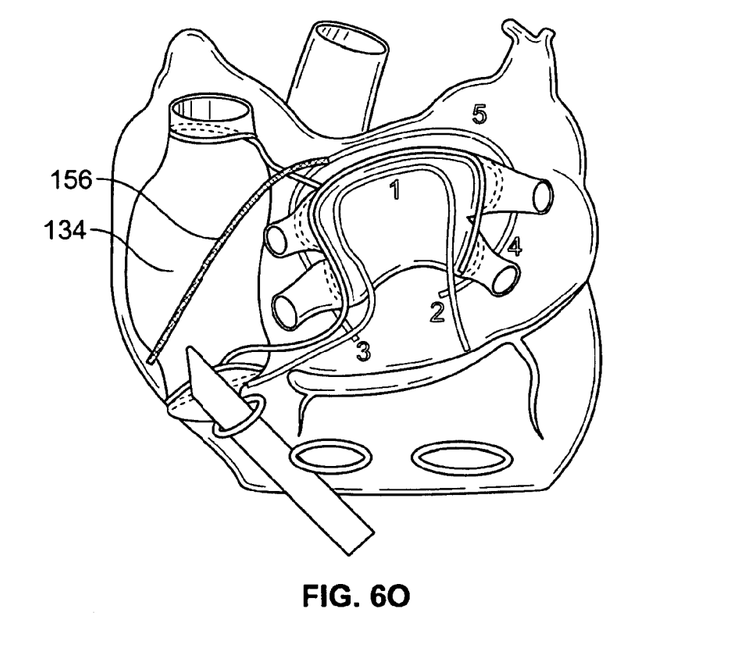
Figure 6P:
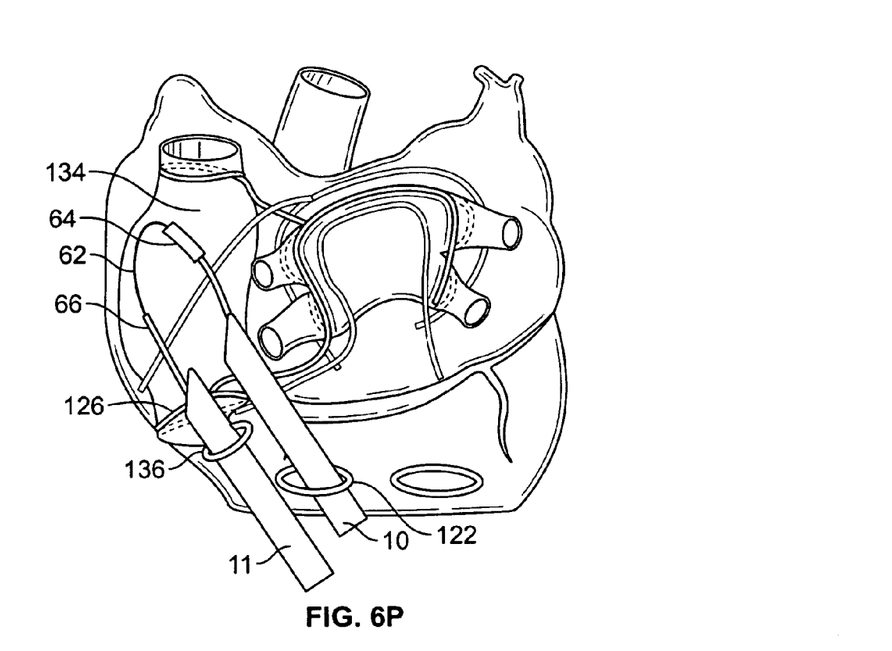
Figure 6Q:
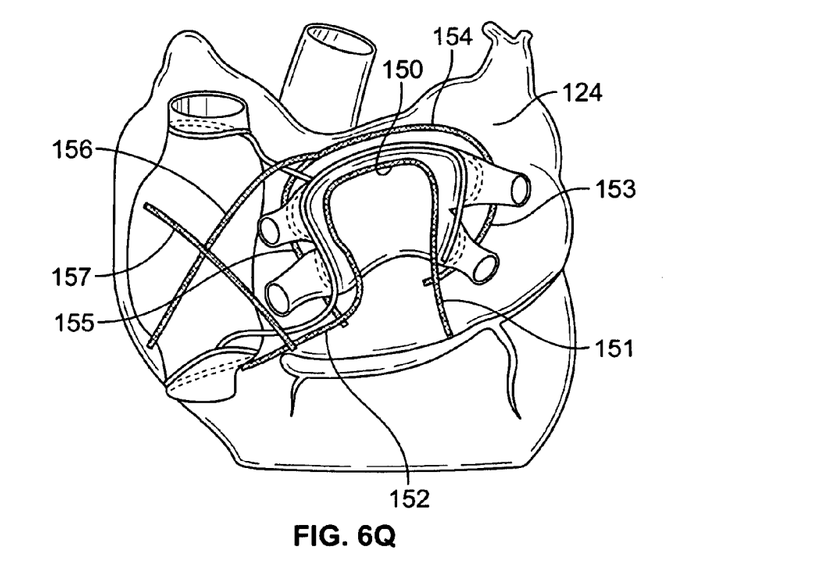

FIGS. 6A to 6Q show one example where the device accesses a posterior surface of the heart 106 and where the multi-mode dissection attributes of the device enable a bi-atrial lesion pattern on a posterior region of the heart. Since the view is from a posterior surface, the notations of right and left are reversed.

As shown in FIG. 6A, the devices 10 are advanced through an epicardium using a left incision 120 and a right incision 122. This allows a distal opening 16 of the devices 10, 11 to be placed into the pericardal space around the left atrium 124.

Next, as shown in FIG. 6B, a catheter 60 (such as a Foley catheter) passes from the right access device 11 to allow a guidewire 62 to be advanced over the left atrium 124. The guidewire 62 is then retrieved into the left cannula 10 using a set of graspers or other similar device. Next, as shown in FIG. 6C, the guidewire 62 passes between the left 11 and right 10 access devices and ultimately extends out of the proximal ends of the access devices 10 11.

Turning now to FIG. 6D, with the guidewire 62 in place, a medical device 64 (such as an ablation device) is advanced over the guidewire 62 and through the right access device 11. The end of the medical device 64 can be optionally viewed with a flexible scope, such as an endoscope or bronchoscope 66 which is also placed over the guidewire 62 from the left access device 10. The medical device 64 can be any energy delivery, ablation, or coagulation device that may be advanced through the access device. Examples of coagulation devices that adhere to irregular contoured surfaces are disclosed below.

The access device 64 can be advanced over the wire 62, to form coagulation lines 150 and 151 on the left atrium (as shown by FIG. 6E). Coagulation line 152 can be created by manipulating the right access device 11 and pulling the device back towards the right access device 11.

FIG. 6F shows repositioning of the right access device 11 with a rigid scope 68 placed therethrough. The combination as well as the features of the device described herein permit dissection through the first pericardial reflection 126 in front of Watterson's groove 128. The scope allows the surgeon to visually navigate through the space as the access device 11 dissects the pericardial reflection 126. This may be accomplished by rotation of the access device 11, which allows a dissection surface to gently dissect the pericardial reflection 126. As shown in FIG. 6G, once through the first pericardial reflection 126, the cannula can advance into Watterson's groove 128 and used to dissect additional tissue to create space for the medical device (coagulation or ablation device). The physician can then advance the access device 11 to further dissect a second pericardial reflection 130 leading into the transverse sinus 132.

FIG. 6H shows a catheter 60 advanced into transverse sinus 132. Once positioned, a larger sized access device 13 or regular cannula can be placed through the left incision 120 for securing a guidewire 62 placed in the Foley catheter (as shown in FIG. 6I). The larger cannula allows both a rigid scope as well as a grasping instrument to be placed within the cannula 13 for viewing and securing the guidewire 62.

FIG. 6J shows the site once the guidewire 62 extends around the pulmonary veins 108 and extends out of the body. The physician can then advance a treatment device 64 over the guidewire 62 from the right incision 122 and a flexible scope 66 advances over the guidewire 62 from the left incision 122. This permits the physician to view the end of the treatment device 64. The physician can then advance treatment device 64 and scope 66 around the guidewire 62 to create coagulation lesions 153, 154, and 155 (in that order, where lesions 153 and 155 cross lesions 151 and 152. This set of lesions, along with lesions 150, 151, and 152 isolates the pulmonary veins from the remainder of the atrium 124 (as shown in FIG. 6K).

Turning now to FIG. 6L, to create lesions on the right atrium 134, the flexible scope 66 can remain within the transverse sinus 132 and the guidewire 62 can be pulled back into the flexible scope—leaving the tip of the guidewire 62 visible to the scope 66. The physician can then advance the scope 66 and guidewire 62 through the pericardial reflection 130 that was previously dissected and over to the right atrium 134.

Next, as shown in FIG. 6M, an access device 11 can be inserted to view and accept the end of the guidewire over the right atrium 134. The access device 11 can be placed either through the previously made right incision 122 or through another higher incision 136 in the pericardium that is over the right atrium 134. The physician then advances the guidewire 62 until an end advances out of a proximal end of the access device 11.

Once the guidewire 62 is accessible from the proximal end of the access device 11, the treatment device 64 can be positioned using the guidewire 62 to create the first coagulation lesion 156 on the right atrium 134 (as shown in FIGS. 6N and 6O)

Next, the physician removes the guidewire 62 from the patient and two access devices 10 and 11 are inserted into either incision in the pericardium 122 or 136. The physician situates the tips of the access devices 10 and 11 over the right atrium 134 as shown in FIG. 6P. The physician may need to further dissect the pericardial reflection 126 on the right atrium with access device 10. Once the physician positions the access devices 10 and 11, the physician passes a guidewire 62 between access devices. A Foley catheter, grasper or any such device (not shown) can be used to assist in passing the guidewire. Once the guidewire 62 forms a loop over the right atrium 134, the physician places the treatment device 64 and the scope 66 through a separate access device 10 and 11. The treatment device 64 and scope 66 can be placed through either access device 10 and 11 depending on the desired location of the coagulation lesion. The physician can then create the final coagulation lesion 157 as shown in FIG. 6R. The final coagulation lesions 156 and 157 each cross the previously made lesions on the left atrium 124 creating the pattern as shown.

The integrated vacuum coagulation probes provided by nContact Surgical, Inc., North Carolina are examples of devices that allow intimate contact specifically between a soft tissue surface and the energy portion of the device. In those examples, the electrode(s) used to transmit energy (radiofrequency or ultrasonic) is capable of heating the soft tissue until achieving irreversible injury making the soft tissue non-viable and unable to propagate electrical impulses, mutate, or reproduce. These integrated vacuum coagulation probe embodiments may be in conjunction with the access devices described herein to treat atrial fibrillation, ventricular tachycardia or other arrhythmia substrate, or eliminating cancer in lung, or other soft thoracic tissue by destroying target cells.

Examples of such probes are disclosed in commonly assigned U.S. publications and patents: US20060009762A1 entitled VACUUM COAGULATION PROBE FOR ATRIAL FIBRILLATION TREATMENT; US20060200124A1 entitled VACUUM COAGULATION PROBES; US20060206113A1 entitled METHODS FOR COAGULATION OF TISSUE; US20060235381A1 entitled VACUUM COAGULATION PROBES; US2006-0293646A1 entitled VACUUM COAGULATION & DISSECTION PROBES; US20070043351A1 entitled VACUUM COAGULATION PROBES; US20080114354A1 entitled VACUUM COAGULATION PROBES; US20080114355A1 entitled VACUUM COAGULATION PROBES; and U.S. Pat. No. 6,893,442 entitled VACUUM COAGULATION PROBE FOR ATRIAL FIBRILLATION TREATMENT; U.S. Pat. No. 7,063,698 entitled VACUUM COAGULATION PROBES; the entirety of each of which is hereby incorporated by reference.

In addition, these integrated vacuum coagulation devices may be used to heat soft tissue along the posterior heart surface resulting in heat-induced contraction of collagen in such tissue thereby resulting shrinking of said soft tissue. For example, heating the mitral valve annulus along the posterior atrio-ventricular groove may induce shrinking of the annulus thereby correcting mitral valve regurgitation. However, it is understood that the invention is not limited to the above described vacuum coagulation probes. Instead, any number of coagulation, ablation, or surgical devices may be used as required.

Although the present methods and devices have been described in terms of the embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims of the invention.

What is claimed is:

1. A method of creating atrial lesion patterns on, a first and second atrial surfaces of a heart of a patient, the method comprising:
   accessing a diaphragm through a first incision in an abdomen of the patient;
   advancing at least a first and second access devices through separate openings in the diaphragm into a thoracic cavity of the patient and into a pericardial space adjacent to the first atrial surface;
   positioning a coagulation device adjacent to the first atrial surface through one of the access devices;
   creating a first coagulation region on the first atrial surface with the coagulation device; and
   creating a second coagulation region on the second atrial surface with the coagulation device.

2. The method of claim 1, further comprising positioning a scope within the thoracic cavity to view the coagulation device.

3. The method of claim 2, where positioning the scope within the thoracic cavity comprises advancing the scope through one of the access devices.

4. The method of claim 1, where advancing at least the first and second access devices through the diaphragm into a thoracic cavity of the patient and into a pericardial space adjacent to the first atrial surface comprises maintaining lungs of the patient in an inflated state.

5. The method of claim 4, further comprising advancing at least the first and second access devices through the diaphragm and adjacent to the first atrial surface without creating an incision in a chest or through a rib cage.

6. The method of claim 1, further comprising dissecting a pericardial reflection with a dissecting surface of the first access device so that a second atrial surface is accessible from the first atrial surface.

7. The method of claim 6, where dissecting of the pericardial reflection comprises inserting a scope into the first access device.

8. The method of claim 6, where dissecting of the pericardial reflection comprises dissecting a first pericardial reflection, advancing the first access device adjacent to a pair of right pulmonary veins and further dissecting a second pericardial reflection adjacent to a transverse sinus of the heart.

9. The method of claim 1, where creating the first coagulation region on the first atrial surface with the coagulation device comprises creating a series of coagulation lines to isolate a right and a left pair of pulmonary veins.

10. The method of claim 1, further comprising withdrawing at least one access device and advancing the access device adjacent to the second atrial surface prior to creating the second coagulation region.

11. The method of claim 6, further comprising creating a third coagulation region across the first and second atrial surfaces and through at least one of the dissected pericardial reflections.

12. The method of claim 11, further comprising advancing the coagulation device from the first atrial surface to the second atrial surface through at least one of the dissected pericardial reflections to create the third coagulation region.

13. The method of claim 6, where dissecting of the pericardial reflection comprises rotating the first access device so that the dissecting surface of the access device gently dissects the pericardial reflection.

* * * * *